US00PP22839P2

(12) United States Plant Patent
Takeuchi

(10) Patent No.: US PP22,839 P2
(45) Date of Patent: Jul. 3, 2012

(54) ***PETUNIA* PLANT NAMED 'KEISURFHOPISES'**

(50) Latin Name: *Petunia×hybrida*
Varietal Denomination: Keisurfhopises

(75) Inventor: Shunsuke Takeuchi, Kozaki-machi (JP)

(73) Assignee: Keisei Rose Nurseries, Inc., Tokyo (JP)

( * ) Notice: Subject to any disclaimer, the term of this patent is extended or adjusted under 35 U.S.C. 154(b) by 36 days.

(21) Appl. No.: 12/927,113

(22) Filed: Nov. 5, 2010

(51) Int. Cl.
*A01H 5/00* (2006.01)

(52) U.S. Cl. ..... Plt./356.22

(58) Field of Classification Search ..... Plt./356.22
See application file for complete search history.

*Primary Examiner* — June Hwu
(74) *Attorney, Agent, or Firm* — C. A. Whealy

(57) ABSTRACT

A new and distinct cultivar of *Petunia* plant named 'Keisurfhopises', characterized by its compact, upright and mounding plant habit; vigorous growth habit; freely branching and flowering plant habit; long flowering period; single light red purple-colored flowers; and good garden performance.

2 Drawing Sheets

Botanical designation: *Petunia×hybrida.*
Cultivar denomination: 'KEISURFHOPISES'.

BACKGROUND OF THE INVENTION

The present invention relates to a new and distinct cultivar of *Petunia* plant, botanically known as *Petunia×hybrida* and hereinafter referred to by the name 'Keisurfhopises'.

The new *Petunia* plant is a product of a planned breeding program conducted by the Inventor in Sawara, Chiba, Japan. The objective of the breeding program is to create new compact and freely flowering *Petunia* plants with early flowering habit and attractive flower coloration.

The new *Petunia* plant originated from a cross-pollination made by the Inventor in September, 2005 in Sawara, Chiba, Japan of an unnamed proprietary selection of *Petunia×hybrida*, not patented, as the female, or seed, parent with an unnamed proprietary selection of *Petunia×hybrida*, not patented, as the male, or pollen, parent. The new *Petunia* plant was discovered and selected by the Inventor as a single flowering plant within the progeny of the stated cross-pollination in a controlled environment in Sawara, Chiba, Japan in March, 2006.

Asexual reproduction of the new *Petunia* plant by terminal cuttings in a controlled environment in Sawara, Chiba, Japan since September, 2008 has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Keisurfhopises'. These characteristics in combination distinguish 'Keisurfhopises' as a new and distinct cultivar of *Petunia* plant:

1. Compact, upright and mounding plant habit.
2. Vigorous growth habit.

3. Freely branching and flowering plant habit.
4. Long flowering period.
5. Single light red purple-colored flowers.
6. Good garden performance.

Plants of the new *Petunia* can be compared to plants of the female parent selection. Plants of the new *Petunia* differ primarily from plants of the female parent selection in the following characteristics:

1. Plants of the new *Petunia* are more compact than and not as spreading as plants of the female parent selection.
2. Plants of the new *Petunia* have smaller flowers than plants of the female parent selection.
3. Plants of the new *Petunia* and the female parent selection differ slightly in flower color.

Plants of the new *Petunia* can be compared to plants of the male parent selection. Plants of the new *Petunia* differ primarily from plants of the male parent selection in the following characteristics:

1. Plants of the new *Petunia* are more compact than plants of the male parent selection.
2. Plants of the new *Petunia* have larger flowers than plants of the male parent selection.

Plants of the new *Petunia* can also be compared to plants of the *Petunia* 'Sunsurfcoparu', disclosed in U.S. Plant Pat. No. 18,141. In side-by-side comparisons conducted in Sawara, Chiba, Japan, plants of the new *Petunia* and 'Sunsurfcoparu' differed primarily in the following characteristics:

1. Plants of the new *Petunia* had smaller flowers than plants of 'Sunsurfcoparu'.
2. Plants of the new *Petunia* flowered for a longer period of time than plants of 'Sunsurfcoparu'.
3. Plants of the new *Petunia* and 'Sunsurfcoparu' differed in flower petal, throat and tube color.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of a typical flowering plant of 'Keisurfhopises' grown in a container.

The photograph on the second sheet is a close-up view of a typical flowering plant of 'Keisurfhopises'.

DETAILED BOTANICAL DESCRIPTION

The aforementioned photographs and following observations, measurements and values describe plants grown during the early summer in 12-cm containers in a glass-covered greenhouse in Yachiyo, Chiba, Japan and under commercial practices. During the production of the plants, day temperatures averaged 22° C. and night temperatures averaged 14° C. Plants were pinched one time and were one month old when the photographs and description were taken. In the following description, color references are made to The Royal Horticultural Society Colour Chart, 2007 Edition, except where general terms of ordinary dictionary significance are used.

Botanical classification: *Petunia×hybrida* 'Keisurfhopises'.

Parentage:

- *Female, or seed, parent*.—Unnamed proprietary selection of *Petunia×hybrida*, not patented.
- *Male, or pollen, parent*.—Unnamed proprietary selection of *Petunia×hybrida*, not patented.

Propagation:

- *Type*.—By terminal cuttings.
- *Time to initiate roots, summer*.—About one week at temperatures of 25° C.
- *Time to initiate roots, winter*.—About three weeks at temperatures of 10° C.
- *Time to produce a rooted young plant, summer*.—About three weeks at temperatures of 25° C.
- *Time to produce a rooted young plant, winter*.—About four weeks at temperatures of 20° C.
- *Root description*.—Fibrous, medium in thickness; light brown in color.
- *Rooting habit*.—Moderate branching; medium in density.

Plant description:

- *Plant and growth habit*.—Compact, upright and mounding plant habit; freely branching habit with numerous lateral branches developing per plant; pinching enhances lateral branch development; vigorous growth habit.
- *Plant height*.—About 15 cm.
- *Plant diameter*.—About 15 cm.

Lateral branch description:

- *Length*.—About 13 cm.
- *Diameter*.—About 2 mm.
- *Internode length*.—About 7 mm.
- *Strength*.—Strong, flexible.
- *Aspect*.—Upright to outwardly; decumbent.
- *Texture*.—Pubescent.
- *Color*.—Close to 144A.

Foliage description:

- *Arrangement*.—Alternate, simple; sessile.
- *Length*.—About 5 cm.
- *Width*.—About 1.5 cm.
- *Shape*.—Elliptic.
- *Apex*.—Narrowly acute.
- *Base*.—Cuneate.
- *Margin*.—Entire.
- *Texture, upper and lower surfaces*.—Pubescent; viscid.
- *Venation pattern*.—Pinnate; reticulate.
- *Color*.—Developing leaves, upper surface: Close to 137D. Developing leaves, lower surface: Close to 138A. Fully expanded leaves, upper surface: Close to 137C; venation, close to 137C. Fully expanded leaves, lower surface: Close to 138A; venation, close to 138A.

Flower description:

- *Flower arrangement and habit*.—Single salverform flowers arising from leaf axils; freely flowering habit with usually numerous flowers per plant; flowers face upright to outwardly.
- *Fragrance*.—Faintly fragrant; pleasant.
- *Natural flowering season*.—Early flowering habit, plants of the new *Petunia* initiate and develop flowers about two to three weeks after planting; long flowering period; flowering commences naturally in mid-March and plants flower continuously throughout the summer until late October in Japan.
- *Flower longevity*.—Individual flowers last about five days on the plant; flowers not persistent.
- *Flower diameter*.—About 3 cm.
- *Flower length (depth)*.—About 2.7 cm.
- *Flower bud*.—Shape: Cylindrical. Length: About 1.5 cm. Diameter: About 2 mm. Color: Close to 145B.
- *Corolla*.—Arrangement: Five petals fused at the base and opening into a flared trumpet. Petal length from throat: About 1.2 cm. Petal width: About 1.4 cm. Petal shape: Roughly spatulate. Petal apex: Cuspidate. Petal margin: Entire; slightly undulate. Petal texture, upper and lower surfaces: Smooth, glabrous; satiny. Throat texture: Smooth, glabrous. Tube texture: Pubescent. Color: Petal, when opening and fully opened, upper surface: Close to N74C; venation, close to N74C. Petal, when opening and fully opened, lower surface: Close to 75C; venation, close to 75C. Throat: Close to 69D; venation, close to 69D. Tube: Close to 69D; venation, close to 69D.
- *Calyx*.—Arrangement: One star-shaped calyx tube with five sepals fused at the base per flower. Sepal length: About 7 mm. Sepal width: About 1 mm. Sepal shape: Narrowly oblong. Sepal apex: Narrowly acute. Sepal margin: Entire. Sepal texture, upper and lower surfaces: Pubescent. Color, upper and lower surfaces: Close to 138A.
- *Peduncles*.—Length: About 1.2 cm. Diameter: About 1 mm. Strength: Strong. Texture: Pubescent; viscid. Color: Close to 144A.
- *Reproductive organs*.—Stamens: Quantity/arrangement: Five per flower. Anther size: About 1 mm by 1.5 mm. Anther shape: Ellipsoidal. Anther color: Close to 155B. Pollen amount: Moderate. Pollen color: Close to 158B. Pistils: Quantity: One per flower. Pistil length: About 1.7 cm. Style length: About 1.6 cm. Style color: Close to 145B. Stigma shape: Transversely ellipsoidal. Stigma color: Close to 143A. Ovary color: Close to 143C. Seeds/fruits: Seed and fruit development have not been observed on plants of the new *Petunia*.

Garden performance: Plants of the new *Petunia* have been observed to have good garden performance and to tolerate rain, wind and temperatures ranging from about 0° C. to about 35° C.

Pathogen/pest resistance: Plants of the new *Petunia* have not been observed to be resistant to pathogens and pests common to *Petunia* plants.

It is claimed:

1. A new and distinct *Petunia* plant named 'Keisurfhopises' as illustrated and described.

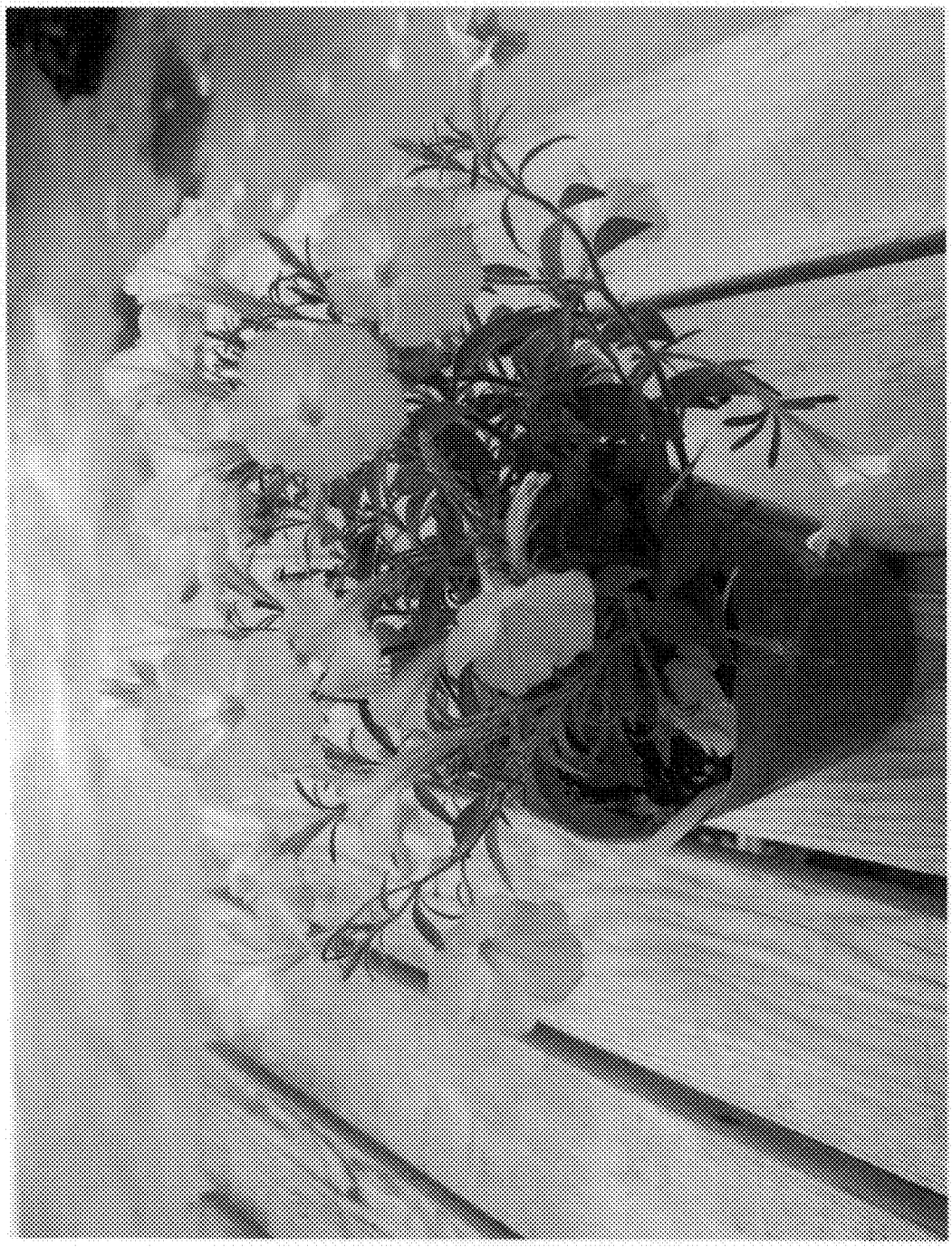

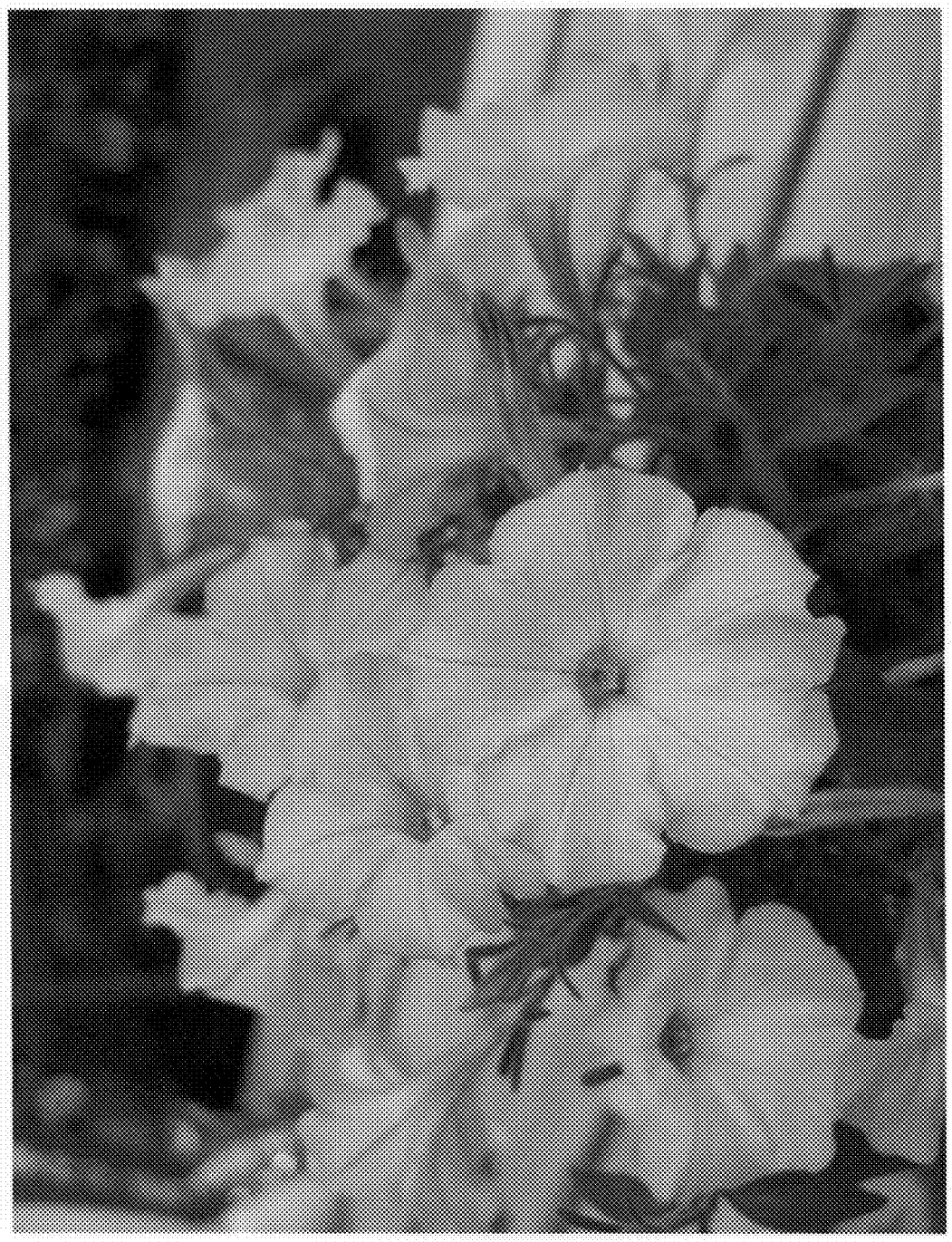

* * * * *